United States Patent [19]

Bradford et al.

[11] Patent Number: Plant 7,506

[45] Date of Patent: Apr. 23, 1991

[54] NECTARINE TREE (SUMMER FIRE)

[76] Inventors: Norman G. Bradford, 11875 E. Savana Rd.; Lowell G. Bradford, 12439 E. Savana Rd., both of Le Grand, Calif. 95333

[21] Appl. No.: 457,232

[22] Filed: Dec. 26, 1989

[51] Int. Cl.[5] ..... A01H 5/00

[52] U.S. Cl. ..... Plt./41

[58] Field of Search ..... Plt./41

[56] References Cited

U.S. PATENT DOCUMENTS

P.P. 3,165 5/1972 Anderson ..... Plt. 41

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described in late July, with first picking on July 22, 1989, making it a mid-seasonal ripening variety. The fruit is uniformly large in size, clingstone in type, dark red in skin color covering almost the entire surface, acidic but sweet in flavor, and exceptionally firm in texture, resulting in excellent quality for keeping and shipping. The variety was developed as a hybridized seedling from the selected seed parent, Red Diamond (U.S. Plant Pat. No. 3,165), and an unnamed seedling as the selected pollen parent.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Summer Fire". The present variety was hybridized by us in 1983, and the resulting seedling was planted in a cultivated area of our experimental orchard at Bradford Farms near Le Grand, Calif. in Merced County (San Joaquin Valley). Specifically, the hybridized seedling was orginated by using Red Diamond (U.S. Plant Pat. No. 3,165) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The present variety most nearly resembles the Summer Bright (U.S. Plant Pat. No. 7,049) by producing fruit that is nearly full red in skin color at maturity, clingstone in type, and extremely firm in texture, but is distinguished therefrom and an improvement thereon by producing fruit that is somewhat larger in size and that ripens nine days later.

The present variety is similar to its selected seed parent, Red Diamond (U.S. Plant Pat. No. 3,165), in fruit appearance by being a full red colored nectarine with excellent firmness, but is distinguished therefrom by ripening twenty-seven days later and by being a clingstone instead of a freestone.

DRAWING

The accompanying photograph exhibits three whole fruits positioned to display the characteristics of the skin color and form, one fruit sliced close to the stone to reveal the flesh, a stone that was cleaned and dried, and branches with leaves, all typical of the subject variety.

POMOLOGICAL CHARACTERISTICS

Referring now more specifically to the pomological characteristics of this new and distinct variety of nectarine tree, the following has been observed under the ecological conditions prevailing at the experimental orchard of the inventors near Le Grand, Merced County (San Joaquin Valley), Calif. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Productive.
Bearing: Regular bearer.
Trunk:
- *Size.*—Medium.
- *Texture.*—Medium.
- *Color.*—Grayish brown [61. gy.Br].
- *Lenticels.*—Numerous. Color: Light yellowish brown [76. 1.yBr]. Average Size: ¼" [6.4 mm.].

Branches:
- *Size.*—Medium.
- *Texture.*—Medium.
- *Color.*—1st year wood — Topside: Grayish red [19. gy.R] if exposed to sunlight. 1st year wood — Underside: Light yellow green [119. 1.YG]. Older wood: Light brown [57. 1.Br].
- *Lenticels.*—Numerous, very small.

Leaves:
- *Size.*—Large. Average length: 6" [152.4 mm.]. Average width: 1⅝" [41.3 mm.].
- *Thickness.*—Medium.
- *Form.*—Elliptical.
- *Apex.*—Acuminate.
- *Base.*—Acute.

*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: 7/16" [11.1 mm.]. Average thickness: 1/16" [1.6 mm.].
*Glands.*—Numbers: Mostly 4 per leaf. Position: Some oppositely and some alternately positioned on petiole and base of blade. Size: Medium. Form: Reniform. Color: Brilliant yellow green [116. brill.YG].
*Stipules.*—Numerous. Average length: 3/16" [4.8 mm.].

Flower buds:
*Hardiness.*—Hardy.
*Size.*—Medium.
*Length.*—Medium.
*Form.*—Free.
*Surface.*—Pubescent.

Flowers:
*Blooming period.*—Medium, as compared with other varieties.
*Size.*—Small.
*Color.*—Moderate pink [5. m.Pk].

FRUIT

Maturity when described: Hard but eating ripe, July 28, 1989.
Date of first picking: July 22, 1989.
Date of last picking: July 30, 1989.
Size: Uniform, large.
*Average diameter axially.*—3" [76.2 mm.].
*Average transversely in suture plane.*—2⅞" [73 mm.].
Form: Uniform, slightly unsymmetrical, slightly oblong.
*Longitudinal section form.*—Oval.
*Transverse section through diameter.*—Round with a slight hump on one side of the suture.
Suture: A shallow depression extending from the base to slightly beyond the apex with a slight depression on both sides of the pistil point.
Ventral surface: Rounded slightly, slightly lipped throughout.
Lips: Slightly unequal.
Cavity: Flaring, circular, suture showing on one side.
Base: Slightly truncate.
Apex: Rounded and slightly depressed.
Pistil point: Some apical and some oblique, very short, depressed within the suture.
Stem: Medium size.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—None observed as of yet.
*Color.*—Mostly dark red [16. d.R] with some very reddish orange [34. v.rO] background color and some light orange yellow [70. l.OY] freckling more prominent toward the apex.
Flesh:

*Color.*—Light yellow [86. l.Y] with some strong red [12. s.R] mottling toward the stone and flecking toward the skin.
*Amygdalin.*—Moderate.
*Juice.*—Abundant, rich.
*Texture.*—Extremely firm, fine, crisp.
*Fibers.*—Abundant, fine, tender.
*Ripens.*—Evenly.
*Flavor.*—Acidic and sweet.
*Aroma.*—Distinct.
*Eating quality.*—Very good.

STONE

Type: Clingstone.
Form: Oblong.
Base: Straight.
Apex: Acute.
Sides: Equal.
Surface: Furrowed toward the apex and along the ventral edge, pitted toward the base.
Ridges: Rounded.
Color: Light brown [57. l.Br].
Pit wall: ¼" [6.4 mm.]thick.
Tendency to split: Very slight.
Kernel:
*Form.*—Oval.
*Taste.*—Sweet.
*Viable.*—Yes.
*Average width.* ½" [12.7 mm.].
*Average length.*—¾" [19.1 mm.].
Skin color: Brilliant yellow [83. brill.Y] before drying.
Pellicle color: Grayish yellowish [80. gy.yBr].
Amygdalin: Scant.

USE

Market: Fresh market, both local and long distance shipping.
Keeping quality: Excellent.
Shipping quality: Excellent.
Resistance to insects: Fruit skin is somewhat susceptible to aphid damage.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of mid-seasonal ripening clingstone nectarine tree, substantially as illustrated and described, which most nearly resembles the Summer Bright (U.S. Plant Pat. No. 7,049) nectarine variety by producing fruit that is nearly full red in color, clingstone in type, and exceptionally firm in texture, but is distinguished from and an improvement on that variety by producing fruit that is somewhat larger in size and that ripens nine days later, thus extending those desirable qualities into a later harvesting and marketing season.

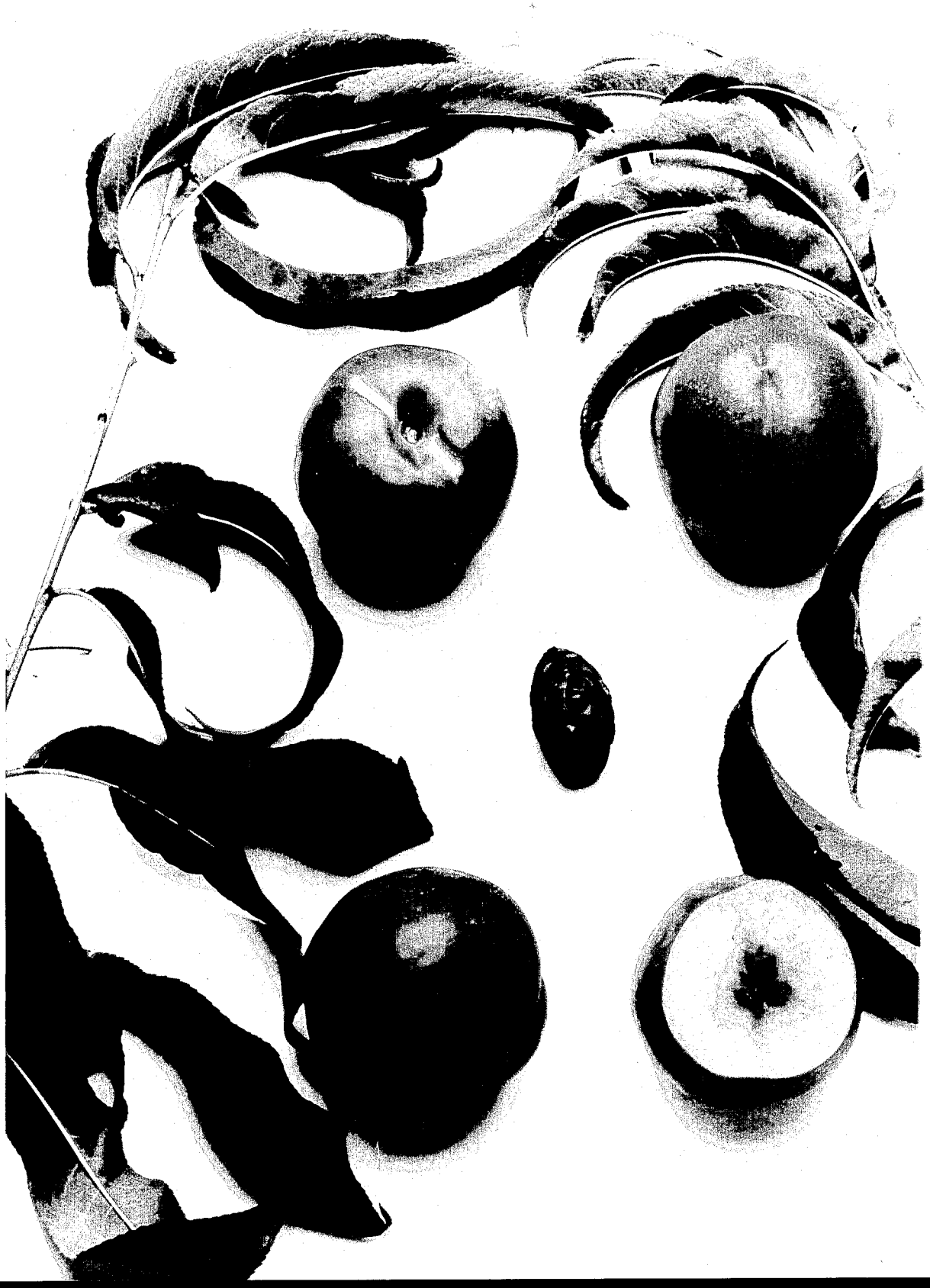

* * * * *